United States Patent [19]

Bird et al.

[11] Patent Number: 5,352,209
[45] Date of Patent: Oct. 4, 1994

[54] BAND FOR ANCHORING A TUBULAR DEVICE TO THE BODY

[75] Inventors: John R. Bird, St. Paul; Michael J. Frazer, Minneapolis, both of Minn.

[73] Assignee: Bird & Cronin, Inc., Minneapolis, Minn.

[21] Appl. No.: 30,563

[22] Filed: Mar. 12, 1993

[51] Int. Cl.$^5$ .............................................. A61M 25/02
[52] U.S. Cl. ............................. 604/179; 128/DIG. 26
[58] Field of Search ....................... 604/174, 179, 180; 128/DIG. 26

[56] References Cited

U.S. PATENT DOCUMENTS

| | | | |
|---|---|---|---|
| 2,449,882 | 9/1948 | Daniels | 604/179 |
| 3,726,280 | 4/1973 | Lacount | 604/179 |
| 3,878,849 | 4/1975 | Muller et al. | 604/179 |
| 4,088,136 | 5/1978 | Hasslinger et al. | 604/179 |
| 4,096,863 | 6/1978 | Kaplan et al. | 604/179 |
| 4,445,894 | 5/1984 | Kovacs | 604/179 |
| 4,569,348 | 2/1986 | Hasslinger | 604/179 |
| 4,591,356 | 5/1986 | Christie | 604/179 |

*Primary Examiner*—Paul J. Hirsch
*Attorney, Agent, or Firm*—Merchant, Gould, Smith, Edell, Welter & Schmidt

[57] ABSTRACT

A band for securing a tube device to a limb or other body member is disclosed. A primary stretchable strap is designed to be secured about a body member at a position therealong at which the tube is to be secured. The primary strap length is adjustable to accommodate body members of varied circumference. A flexible secondary strap designed to retainably engage the tube is secured to and aligned with the primary strap. The secondary strap has a non-stretchable portion that forms a seat for the tube and a stretchable portion, both of which are coated with high-friction material. The tube is enveloped between the lower seat and the upper stretchable portion of the secondary strap, which is pulled and folded in overlying engagement with the tube, and is held in such configuration by Velcro-type fastener means that releasably engages the primary strap.

14 Claims, 1 Drawing Sheet

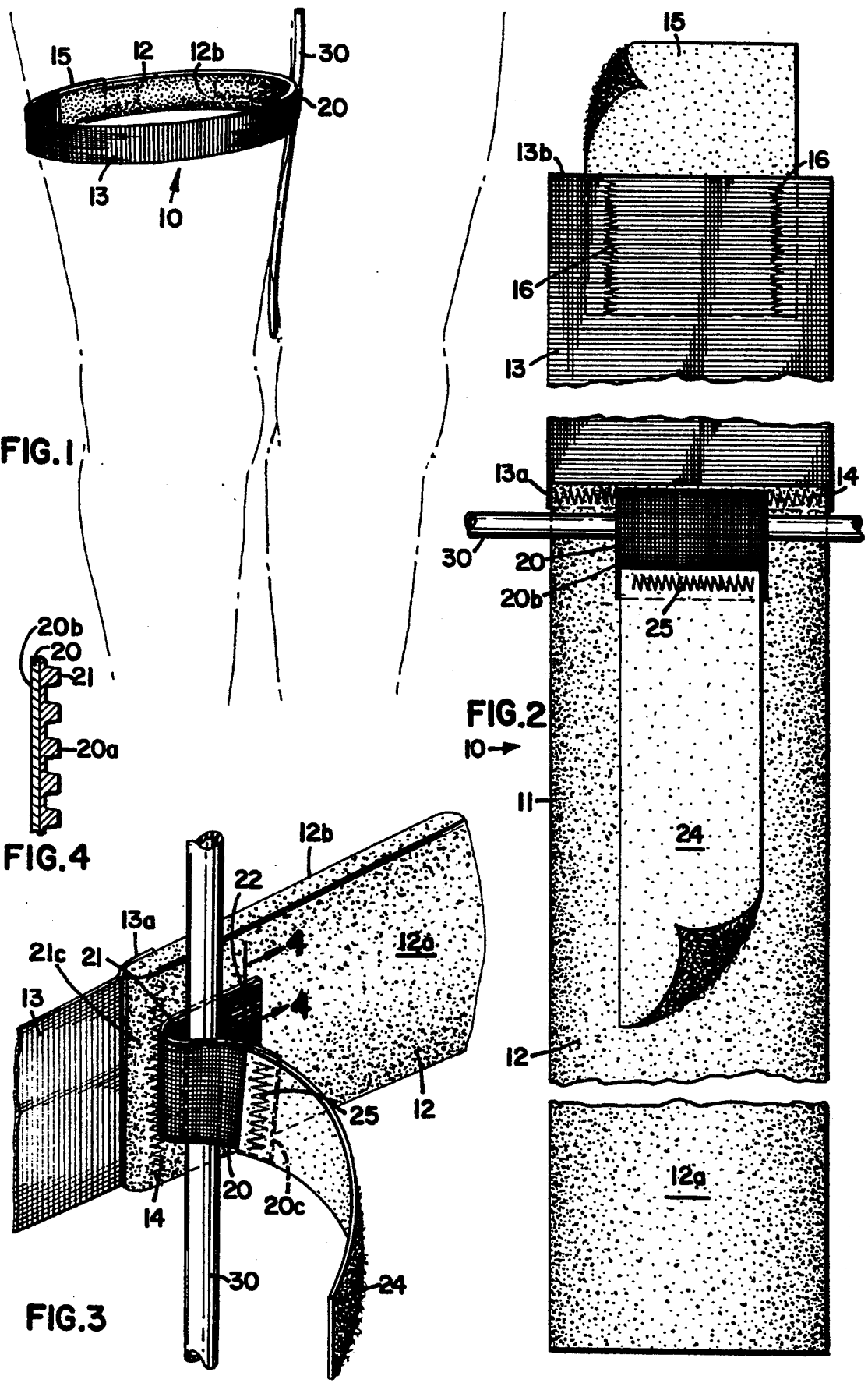

BAND FOR ANCHORING A TUBULAR DEVICE TO THE BODY

FIELD OF THE INVENTION

This invention relates generally to medical accessories and more particularly to an apparatus for securing a catheter or other tube-like member to a limb of a human.

BACKGROUND OF THE INVENTION

There are many instances in which it is desirable to retain or hold a tube-like member in generally fixed position relative to a limb, such as an arm or leg, of a human. The most obvious need arises in hospitals or other patient care facilities. However, any number of situations exist wherein it is necessary or preferable for a tube-like member to be maintained in a fixed or secure position relative to the body so as not to become caught or snagged during movement or activity, or so as not to slip into a position wherein the tube could be bent or crimped or otherwise damaged.

Examples of such applications might include patient-care catheter tubes or intravenous tubes. Such tubes must be positioned so as not to be bent, pinched, crushed, snagged or pulled by movement of the patient or by those administering to the patient.

A number of techniques and apparatus have been used in the past to address the problem. The tube can be directly taped to the patient. However, such taping is not particularly comfortable to the patient and does not lend itself readily to replacement or servicing of the tube. Besides, the tape can leave undesirable residue on the tube and on the patient's body.

A commonly used non-tape retainer has been an adjustable strap member configured for attachment to the leg or arm of the patient, as described in U.S. Pat. No. 4,096,863. The retaining band of such structure includes a rigid metal clip or buckle through which a secondary strip of material passes, to form a loop that can be retainably tightened around a catheter tube or the like, for holding the tube in position against the band. Such structure provides improved flexibility for use with patients of varied size limbs and for use with tubes of varied outer circumference. However, the rigid clip or buckle of such device adds to the cost of the device, and permits slippage of the tube relative to the strap if not tightened enough, or undesirable bending and restriction of the tube, if tightened too much. Further, the presence of the rigid metal clip can cause discomfort to the wearer and can be difficult to secure since the tube retaining tab must be threaded through the clip or buckle in order to secure the tube.

The present invention addresses the above shortcomings of prior art retaining straps and generally provides an improvement over such prior art devices. The retaining strap of the present invention eliminates the rigid metal clip or buckle of the prior art, making it easier to manufacture, less expensive, more convenient to use, and more comfortable for the patient. Further, the retaining strap of the present invention minimizes the chance of damage or bending or crimping of the tube being held thereby.

SUMMARY OF THE INVENTION

This invention provides a very user friendly and efficient retainer strap or band for holding a tubular device in place relative to a limb or body member of a patient, which is also very comfortable to the patient. The present invention uses no buckles for providing the retaining function and does not require the retaining member to be passed or inserted through any holes or slots in the band or strap structure in order to accomplish the retaining function. The tube retaining or holding mechanism is carried by a primary band or strap that incorporates an infinitely adjustable Velcro fastener technique which permits the primary band to be sized upon application to the patient, to the unique size and shape of the body member to which it is being applied. The primary support band includes an elastic portion which enables the band to be secured at the proper tension, as dictated by the patient to which it is being secured. Once the primary support band has been properly positioned on the limb or body member of the patient, the tube member to be secured is simply seated upon the frictional material of the tube retainer portion and is rapidly secured thereto by a simple one-motion step which stretches the tube retaining material while placing it in secure engagement with the tube. The tube retaining strap portion is firmly retained in engagement with the tube by means of a Velcro fastener tab that is sized for ease of handling by the attendant and for facilitating stretching of the retaining material.

According to one aspect of the invention, there is provided a band for anchoring a catheter or other tubular device to a body which comprises:
(a) an extendible primary strap adapted to encircle the portion of the body to which the device is to be anchored;
(b) fastening means connected to the primary strap for securing it in place on the body;
(c) a secondary strap made of stretchable flexible material and having a length approximating the circumference of the device to be secured, wherein the secondary strap has at least one broad surface of resilient high friction material and is configurable to engage and form a loop about the periphery of the device;
(d) means for securing a first length of the secondary strap adjacent one end thereof to the primary strap intermediate its ends and in longitudinal alignment with the primary strap such that the high friction material of the secondary strap faces outward or away from the body;
(e) fastening tab means connected to and continuously extending from the unsecured end of the secondary strap for buckleless releasable securement to the primary strap when the secondary strap is configured in a loop wherein the fastening tab means is significantly longer than the secondary strap to enable ease of user grasp for longitudinally stretching the secondary strap; and
(f) wherein the resilient high friction material of the secondary strap engages approximately two-thirds or more of the outer circumference of the device retained thereby when the fastening tab means is operatively secured to the primary strap.

According to a further aspect of the invention, the high friction material of the secondary strap is made of natural rubber, and preferably has spaced ribs extending longitudinally of the secondary strap. According to yet another aspect of the invention, the primary strap has a first section of non-stretchable material and a second section of stretchable material secured to and longitudinally extending from one end of the first section, and wherein the fastening means is connected to the unsecured end of the second section of the primary strap and preferably comprises a Velcro-type fastener.

According to yet another aspect of the invention, there is provided an appliance for securing a tube or the like along a patient's body member, comprising:
  (a) first strap means for encircling a body member to which a tube is to be secured;
  (b) fastening means for releasably securing the first strap means to the body member;
  (c) second strap means longitudinally aligned with and secured to the first strap means for retainably engaging and securing the tube to the first strap means, wherein the second strap means comprises:
    (i) a first portion of high friction material affixed in non-stretchable manner to an outer surface of the first strap means and forming a lower seat for the tube to be secured;
    (ii) a second portion of elastic high friction material continuously extending from the first portion to a distal end and configured to be stretchably engaged in loop configuration over the tube when seated on the first portion, so as to engage a substantial portion of the tube's outer circumference; and
    (iii) fastener means extending from the distal end of the second portion for urging the distal end of the second portion toward the first strap means in buckleless manner, thereby retainably enveloping the tube between the first and second portions of the second strap means.

While the invention will be described with respect to its application for holding a catheter strap, the invention is not limited to such application. Further, while the invention will be described with respect to specific types of materials and with respect to particular sizes of the various components of the preferred embodiment, it will be understood that the invention is not to be so limited to the described materials or their preferred embodiment sizes. These and other features of the invention and modifications thereof will become obvious to those skilled in the art in view of a more detailed description thereof.

BRIEF DESCRIPTION OF THE DRAWING

Referring to the Drawing, wherein like numerals represent like parts throughout the several views:

FIG. 1 is a fragmentary perspective view of a leg of a human, to which a preferred embodiment of the invention is secured and which illustrates the manner in which the invention may be used to secure a catheter along the leg;

FIG. 2 is a plan view of the outer surface of the band shown in FIG. 1;

FIG. 3 is an enlarged perspective view of that portion of the band of FIG. 2 which engages the tube-like member to be retained thereby, illustrating the fold-over tab portion thereof as it is being retainably looped over the tube-like member; and FIG. 4 is a cross-sectional view generally taken along the line 4—4 of FIG. 3.

DETAILED DESCRIPTION OF THE INVENTION

The tube retaining band or appliance of the present invention is generally illustrated at 10 in the figures. The band 10 has a primary strap portion 11 sized to encircle the limb or body portion to which a tube device 30 is to be secured. The primary strap 11 is constructed of first and second sections 12 and 13 secured end-to-end, as illustrated in FIGS. 2 and 3. Section 12 is constructed of non-stretchable material. In the preferred embodiment, the first section 12 has an upper fabric 12a made of a looped material typically woven of cotton of the velvet type, having loops extending outwardly from the outer face of the first section 12. The inner surface of the first section 12, which directly engages the limb or other member encircled by the tube-retaining band, is in the preferred embodiment, constructed of a soft foam lining material 12b that is integrally bonded to the outer looped material 12a along the entire length of the first section 12 of the material.

The second section 13 of the primary strap 11 is made of an elastic webbing material which is stretchable in a lengthwise direction, but has a relatively fixed dimension across its width. The inside surface of the webbing 13 carries a soft lining material (not illustrated) which may be in the form of a Helanca backing or other soft material which is comfortable to the skin, but which does not interfere with the lengthwise elasticity of the second section webbing material. One end 13a of the second section 13 is securely stitched at 14 to a corresponding end 12c of the first section 12, to form a continuous primary strap 11. In the preferred embodiment, when the primary strap portion is used for the purposes of retainably holding a catheter, the width of the primary strap portion 11 is approximately two inches, and the first and second sections 12 and 13 thereof are each approximately 12 inches long in an unstretched configuration. A short strip of "hook" Velcro-type inelastic fastening material 15 is secured by stitching 16 to the inner or lining side of the second section 13 of the primary strap 11, at a second end 13b thereof. The Velcro-type fastening material is oriented relative to the primary strap portion 11 such that its hook-like barbs face away from the inner lining of the second section 13 such that when the primary strap 11 is wound about a limb, the foam lining 12b of the first section 12 and the lined inner surface of the second section 13 comfortably engage the patient's skin, and the strap encircles the limb with the fastening end 15 overlapping the outer looped portion 12a of the first section 12. When applied in this fashion, the Velcro strip hook members face the looped fabric 12a of the first section 12, to releasably engage the outer surface of the first section 12. Because the second section 13 of the primary strap 11 is stretchable, the attendant can apply the primary strap portion 11 to the patient with sufficient tension so that the limb is firmly gripped by the band and held in place, but without applying so much pressure to the limb so as to cut off circulation. Further, since the Velcro hook portion 15 of the primary strap may be secured at any position along the outer looped material 12a of the first section 12, the primary strap portion 11 is continuously adjustable along the length of the first section 12 and as permitted by the longitudinal expansion of the second section 13.

The primary strap portion 11 provides the location along the patient's limb at which the catheter or other tube-like member will be secured to the patient's body. Actual securement of the catheter 30 is provided by means of a secondary strap portion 20. The width of the secondary strap portion 20 may be significantly less than that of the primary strap portion 11, and is in the preferred embodiment, approximately one inch wide. Its length may vary, but need only be long enough to encircle the circumference of the tube 30 being retained thereby. In the preferred embodiment, the nominal unstretched length of the secondary strap 20 is approximately two inches. The secondary strap portion 20 is configured of an elastic webbing material which is stretchable in a lengthwise direction but has a relatively fixed width dimension, similar to that of the second section 13 of the primary strap 11, but of significantly thinner material. The "inside" surface (generally indicated at 20a of the secondary strap portion 20) carries a soft lining material which moves with and does not interfere with the elasticity of the secondary strap; whereas the "outer" surface (generally indicated at 20b) can comprise a harder surface. The inner surface 20a is also entirely or partially lined with a layer of rubber material 21. The rubber material may either be of solid or ribbed cross-sectional configuration. In the preferred embodiment, the rubber material 21 is of ribbed configuration (FIG. 4), wherein the ribs extend longitudinally of the secondary strap 20 and is generally referred to as latex tracking. The secondary strap portion material of the preferred embodiment is generally referred to as a woven knit elastic latex tracking comprising 92% nylon or polyamide material, 8% elastomer or lycra material and has a 100% natural rubber inner lining 21.

The secondary strap portion 20 is secured (in the preferred embodiment) by stitching 22 to the first section 12 of the primary strap 11 adjacent its first end 12c that is secured to the second section 13 of the primary strap 11. A longitudinal length "x" of the secondary strap portion 20 of greater or equal to the diameter of the tube 30 to be secured, is stitched to the first section 12 of the primary strap 11 and forms a base or seat for the tube 30 to be secured. Since the first section 12 does not stretch in the longitudinal direction, the "x" length of the secondary strap which is stitched to the primary strap also does not stretch in operative use.

A second length of "hook" Velcro-type inelastic fastening material 24 is secured by stitching 25 to the outer surface 20b of the secondary strap 20 at its free or distal end 20c. The second Velcro fastener material 24 is oriented relative to the secondary strap 20 such that its hook-like barbs face in the same direction as the inner surface 20a of the secondary strap 20 such that when the free or distal end 20c of the secondary strap 20 is folded back toward the first section of the primary strap (as indicated in FIGS. 2 and 3) the hook members cooperatively address and are permitted to operatively releasably engage the looped outer surface 12a of the first section 12 of the primary strap 11. In the preferred embodiment, the width of the second Velcro fastener 24 is the same as that of the secondary strap portion 20, and has a length of approximately three inches which permits a user of the apparatus to easily grasp and pull on the fastener 24 to stretch the secondary strap 20. However, it will be understood by those skilled in the art, that the dimensions of the fastener 24, as well as those of the other strap portions of the invention could assume any number of different sizes.

To secure a catheter or other tube-like member 30 to the limb or other portion of the wearer's body, the primary strap portion 11 is placed around the limb as illustrated in FIG. 1, with the lined surface 12b in engagement with the limb. The primary strap portion is longitudinally adjusted relative to the limb such that the secondary strap portion 20 attached thereto is aligned with that portion of the limb at which the tube 30 is to be secured. By holding the first section 12 of the primary strap in such position, and by extending the elastic second section 13 to encircle the limb at the desired tension, and by engaging the hooked fastener 15 to the outer surface 12a of the first section 12 of the primary strap 11, the primary strap is operatively secured to the wearer's limb. The tube 30 to be secured is placed across and seated upon the secured length "x" of the rubber lining 21 of the secondary strap portion 20 (as illustrated in FIG. 3). The tube 30 is secured, as positioned, to the primary strap 11 by pulling on the second Velcro fastener 24 so as to longitudinally stretch the secondary strap 20 and by folding and entraining the stretched secondary strap 20 back over the tube 30 to form a loop which compressibly encircles the tube 30, and by securing the second Velcro fastener 24 to the upper surface 12a of the first section 12 of the primary strap 11 so as to retain the stretched condition of the secondary strap 20. In such position, the secondary strap 20 will firmly retainably engage and hold the tube 30 in position against the primary strap 11 as illustrated in FIG. 2, without crimping, bending or damaging the tube 30. The elasticity of the secondary strap 20 and the frictional engagement of its rubber lining 21 provide snug retaining engagement of the tube 30, but allow the tube 30 to be manually adjusted in its longitudinal direction after fastening, if so desired.

Due to the relatively short length of the secondary strap portion, the second Velcro fastener 24 will engage the primary strap in close proximity to the retained tube 30, thereby forcing the proximal end of the secondary strap toward retaining engagement with the tube. With this configuration approximately two-thirds or more of the outer circumferential area of the tube is engaged by the rubber lining of the secondary strap, providing a secure, yet safe engagement of the tube.

While the invention has been described with respect to its application as illustrated in the preferred embodiment, it will be understood that a number of variations of such embodiment and its applications for use with devices other than a catheter are possible. Such modifications of the invention will become apparent to those skilled in the art in light of the foregoing description. This description is intended to provide a specific example of an embodiment which clearly distinguishes and discloses the principles of the invention. All alternatives, modifications and variations of the present invention that fall within the broad scope of the appended claims are covered.

What is claimed is:

1. A band for anchoring a catheter or other tubular device to a body, comprising:

(a) an extendible primary strap adapted to encircle the portion of the body to which the device is to be anchored;

(b) fastening means connected to the primary strap for securing it in place on the body;

(c) a single secondary strap made of stretchable flexible material and having a length approximating the circumference of the device, said secondary strap having at least one broad surface of raised resilient high friction material and being configured to engage and form a loop about the periphery of the device;

(d) means for securing a first length of said secondary strap adjacent one end thereof to said primary strap intermediate its ends and in longitudinal alignment therewith, such that said high friction material of said secondary strap faces outward from the body;

(e) fastening tab means connected to and continuously extending from the unsecured end of said secondary strap, for buckleless releasable securement directly to the primary strap when said secondary strap is configured in a loop, said fastening tab means being relatively longitudinally unstretchable and significantly longer than said secondary strap to enable ease of user grasp for longitudinally stretching said secondary strap; and (f) wherein said resilient high friction material of said secondary strap engages approximately two-thirds or more of the outer circumference of the device retained thereby when said fastening tab means is operatively secured to said primary strap.

2. A band as recited in claim 1, wherein said broad surface of said secondary strap high friction material comprises a natural rubber material.

3. A band as recited in claim 2, wherein said rubber material includes spaced ribs extending longitudinally of said secondary strap.

4. A band as recited in claim 1, wherein said fastening tab means comprises a hook fastener material, and wherein the surface of said primary strap engaged by said fastening means comprises a complementary looped material.

5. A band as recited in claim 1, wherein said primary strap comprises a first section of non-stretchable material and a second section of stretchable material secured to and longitudinally extending from one end of said first section; and wherein said fastening means is connected to the unsecured end of said second section of said primary strap.

6. A band as recited in claim 5, wherein said fastening means comprises a Velcro-type hook material that cooperatively releasably engages that surface of said first section of said primary strap that is disposed away from the body it encircles.

7. A band as recited in claim 6, wherein said fastening means is operatively engagable with said primary strap at an infinite number of positions along the length of said first section.

8. A band as recited in claim 5, wherein said first length of said secondary strap is secured to said primary strap adjacent said one end thereof, and in a manner such that when said secondary strap is operatively formed into a loop about the periphery of the device, said tab means operatively engages said first section of the primary strap.

9. A band as recited in claim 8, wherein said fastening tab means comprises a hook-fastener material, and wherein the surface of said first section of said primary strap engaged by said fastening tab means comprises a complementary looped material.

10. An appliance for securing a tube or the like along a patient's body member, comprising:

(a) a first strap means for encircling a body member to which a tube is to be secured;

(b) fastening means for releasably securing said first strap means to said body member;

(c) a single second strap longitudinally aligned with and secured to said first strap means for retainably engaging and securing said tube to said first strap means, comprising:

(i) a first portion of resilient high friction material affixed in non-stretchable manner to an outer surface of said first strap means, and facing outward from the body forming a lower seat for the tube to be secured;

(ii) a second portion of resilient elastic high friction material continuously extending from said first portion to a distal end and configured to be stretchably engaged in loop configuration over the tube when seated on said first portion, so as to engage a substantial portion of the tube's outer circumference; and (iii) fastener means longitudinally extending from the distal end of said second portion for urging said distal end of said second portion toward said first strap means for direct releasable securement to said first strap means in buckleless manner, thereby retainably enveloping said tube between said first and said second portions of said second strap means, said fastener means having a length substantially longer than that of said combined first and second portions of said second strap means, thereby enabling ease of user grasp for longitudinally stretching said second portion about said tube.

11. An appliance as recited in claim 10, wherein said fastener means comprises Velcro-type hook material.

12. An appliance as recited in claim 11, wherein said first strap means comprises a first section of non-stretchable material and a second section of stretchable material secured to and longitudinally extending from one end of said first section; and wherein said fastening means is connected to the unsecured end of said first strap means.

13. An appliance as recited in claim 12, wherein said fastening means comprises a Velcro-type hook material that cooperatively releasably engages that surface of said first section of said first strap means that is disposed away from the body member.

14. An appliance as recited in claim 12, wherein said first portion of said second strap is secured to said first section of said first strap adjacent said one end thereof, and in a manner such that when said second strap is operatively formed into a loop about the periphery of the tube, said fastener means operatively engages said first section of said first strap.

* * * * *